United States Patent [19]
Pajalich

[11] Patent Number: 5,267,555
[45] Date of Patent: Dec. 7, 1993

[54] APPARATUS AND METHOD FOR IONIZING MEDICATION CONTAINING MISTS

[76] Inventor: Philip Pajalich, 4955 East First St., Tucson, Ariz. 85711

[21] Appl. No.: 950,837

[22] Filed: Sep. 24, 1992

Related U.S. Application Data

[63] Continuation-in-part of Ser. No. 594,285, Oct. 9, 1990, abandoned, which is a continuation of Ser. No. 214,511, Jul. 1, 1988, abandoned.

[51] Int. Cl.$^5$ .............................................. A61M 11/00
[52] U.S. Cl. .............................. 128/200.14; 128/202.25
[58] Field of Search .................. 128/200.14, 202.23, 128/202.25

[56] References Cited

U.S. PATENT DOCUMENTS

| | | | |
|---|---|---|---|
| 3,194,236 | 7/1965 | Wehner | 128/202.25 |
| 3,232,292 | 2/1966 | Schaefer | 128/202.25 |
| 4,196,727 | 4/1980 | Verkaart et al. | 128/202.23 |
| 4,369,776 | 1/1983 | Roberts | 128/202.25 |

OTHER PUBLICATIONS

"A Body Current Activated Circuit Breaker" by Kremer et al. IEEE Transactions on Biomedical Engineering Sep. 1975, p. 418.

*Primary Examiner*—Edgar S. Burr
*Assistant Examiner*—Aaron J. Lewis
*Attorney, Agent, or Firm*—Joseph G. Nauman

[57] ABSTRACT

A method for administering medication to a patient by inhalation of an ionized aerosol mist of medication particles includes ionizing the particles by passing the mist through a passage containing a pointed electrode energized to 1,000 to 50,000 volts DC. Apparatus for use in performing the method includes a grounding electrode on the ionizer for (a) grounding the patient relative to the high potential of the pointed electrode, to place the patient's respiratory tissue at ground potential relative to the charged aerosol particles, or (b) establishing a tightly defined ion field within the apparatus whereby ions not attached to the aerosol particles will return to ground and not cause a build up of static charge in/on the patient/user. Contact rings on the ionizer may be connected to a current limiting device so as to prevent harmful electrical shock to a person coming into contact with the energized pointed electrode.

8 Claims, 4 Drawing Sheets

APPARATUS AND METHOD FOR IONIZING MEDICATION CONTAINING MISTS

CROSS-REFERENCE TO RELATED APPLICATIONS

This application is a continuation-in-part of U.S. application Ser. No. 07/594,285 filed Oct. 9, 1990, which is in turn a continuation of U.S. application Ser. No. 07/214,511 filed Jul. 1, 1988 both now abandoned.

BACKGROUND OF THE INVENTION

The invention relates to apparatus and methods for applying a large DC voltage to an electrode to ionize medication-containing mist in order to improve effectiveness of a dosage of the medication to a mammalian patient.

Quite a variety of aerosol dispensers have been provided for distributing or concentrating a fine mist or aerosol of medicated liquid which is used in treatment of illnesses that respond to the inhalation/application of such medications. For example, in treatment of asthma there are many such medications which can be effectively administered by inhalation techniques to inhibit or diminish the respiratory problems of the asthma affected patient. There has been recognition in the prior art of potential benefit from electrically ionizing medicated mist as administered. U.S. Pat. No. 3,502,077 discloses a device in which DC potentials of 20 to 100 volts are applied to "accelerator rings" disposed in a pipe through which a medicated aerosol is passed. U.S. Pat. No. 4,369,776 ionizes water vapor with high voltage pulses across an electrode gap within a tube carrying water vapor; the apparatus is used for dermatological purposes and is referred to as a "dermatological ionizing vaporizer." U.S. Pat. No. 3,194,236 applies a DC voltage of 4,000 to 40,000 volts to liquid which is then converted into an aerosol; in one embodiment described, a charging screen with 100 volts applied thereto is paced in the path of the charged aerosol. U.S. Pat. No. 4,310,474 discloses a device in which a charged vapor stream, for utilization in industrial applications, electrostatically controls a flow of the charged droplets so as to meter them into a vaporizer.

It is known that the unique physiology of the mammalian (particularly human) lung includes a quite substantial effective surface area, including many interstices and linked passages, and any medicated particles or mist droplets entering the lung as an aerosol must pass through these varying linked passages to reach all (or as much as possible) of the effective surface area for maximizing treatment from a given application of the medicated aerosol. None of the devices disclosed in the aforementioned prior patents enable medicated aerosol mist droplets to effectively reach and adhere to all (or nearly all) of the effective surface area of the patient's lungs.

Aerosolized medication can be used in either dry or wet form. The so-called standard metered dose inhalers (MDIs) use Freon or the like as a propellant for powdered medication having a particle size in the order of 2 microns. Also, liquid medications (usually much stronger) can be combined with water and/or a saline solution in a nebulizer device to produce a so-called wet aerosol (e.g., a mist containing liquid medication droplets) which can be administered to a patient, allowing a practitioner to use stronger dosages of medication if desired.

SUMMARY OF THE INVENTION

The invention, in accordance with the preferred embodiment, provides a method and an apparatus for preparing and administering doses of medication particles or mist, to a mammalian patient by inhalation. A high voltage is applied to an elongated pointed electrode extending into a passage of an ionizing device, extending from an inlet to an outlet of the ionizing device. The flow of medication particles or mist is passed through the inlet, and by the pointed tip of the electrode, and simultaneously a DC potential, in the range of 1,000 to 50,000 volts, is applied to the electrode and acts to ionize the medication mist which is then (substantially immediately) inhaled by the patient. The patient is effectively electrically grounded relative to the highly charged medication particles which emanate from the device and pass into the patient's respiratory system. Preferred embodiments employ application of positive high voltage potential to the electrode while the patient's body is at ground potential; however, it is the high potential difference which is of importance, and the electrode can be charged to a high negative potential with the patient at ground potential. In one embodiment, the patent may conveniently be electrically grounded via a conductive cover or coating of the ionizing device, which the patient holds near to his/her mouth to effectuate inhaling of the medication dosage. In another embodiment, the medication aerosol particles are highly charged by flowing them in a gas stream through a tightly defined ion (charging) field internally of the ionizing device. Here, an internal grounded ring is supported in closely spaced position around the high potential electrode, and the medication aerosol is caused to flow around the high voltage electrode and through the grounded ring. The highly charged aerosol particles (wet or dry) are then expelled into the patient's respiratory system. In this embodiment, it is not necessary physically to ground the patient vis-a-vis the high voltage generator, since the patient's natural grounded state will be sufficient, taking into account the high differential existing between the patient and the charged medication particles and the fact that the ground ring avoids build up of a static charge in the patient during use of the device.

This method, and the apparatus for performing the method, have been found in actual testing to cause a thorough penetration of the mammalian lung by the aerosol medication, with effective application of the particles/droplets onto a very large area of the lung tissue thus exposed to the inhaled medication. This results not only in more effective application of the medication, but also allows more effective treatment with lower dosages, and thus potential minimizing of known side-effects of such medications.

Accordingly, it is the principal object of the invention to provide such a method and apparatus which effectively ionizes and applies aerosol mist medications which are inhaled by a mammalian patient, to minimize waste of the medication, to reduce the size of dosage required for patient relief from respiratory distress symptoms, and to disperse such medications more effectively and uniformly into the mammalian lung; another object of the invention is to provide such method and apparatus which enable deep and thorough penetration of aerosol mist medication into all areas of the lungs of a mammal and adherence of medication droplets to the majority of the lung surface tissue.

Other objects and advantages of the invention will be apparent from the following description, the accompanying drawings and the appended claims.

DESCRIPTION OF THE PREFERRED EMBODIMENTS

Figure 1:
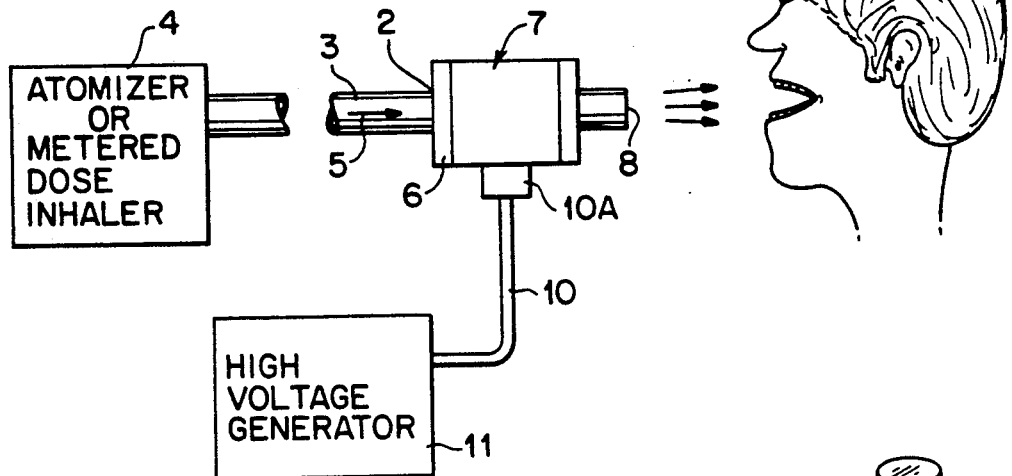
FIG. 1 is a diagram of the apparatus of the invention.
Figure 3:
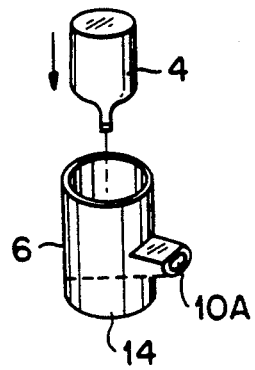
FIG. 3 is a perspective view of a metered dose inhaler (MDI) in which an ionizing apparatus similar to the apparatus of FIG. 2 can be included.

Referring to the drawings, the mist or aerosol ionizing apparatus 1 includes an inlet 2 connected by tube 3 to the outlet of an atomizer or metered dose inhaler (MDI) 4, hereafter simply referred to as the atomizer, which can be any suitable commercially available device which atomizes liquid medication. Various commercially available atomizers (sometimes called nebulizers) are known and quite often connectable to the inspiratory hose of a ventilator or other inhalation apparatus for patient treatment.

The ionizing device is provided with an outlet tube 8, which can be directed into the mouth of the patient, as graphically illustrated in FIG. 1. The medicated aerosol or mist enters the ionizing device via inlet tube 3, as indicated by arrow 5, passes through the chamber 28 of the ionizer (see FIG. 2), and emerges through outlet tube 8 as ionized medicated mist or aerosol which is then immediately inhaled by the patient. The diameter of passage 28 is not critical, and may be typically be in the order of ¾ inch. The medicated mist is passed to the lungs of the patient, propelled by a combination of the expelling force of the atomizer and the patient's own inhalation effort.

The ionizing device 1 has a body 6, the interior of which defines passage 28, formed of an electrically insulative material, and has an electrically conductive covering 7 or much or all of its exterior which provides a convenient electrical contact with the patient who may grasp the device in his/her hand, for the purpose of establishing a common electrical ground for both ionizing device 1 and the patient. Thus, covering 7 function as a ground electrode. Other alternative ways of electrically grounding the patient relative to the ionizing device will be apparent to those skilled in the art.

Figure 2:
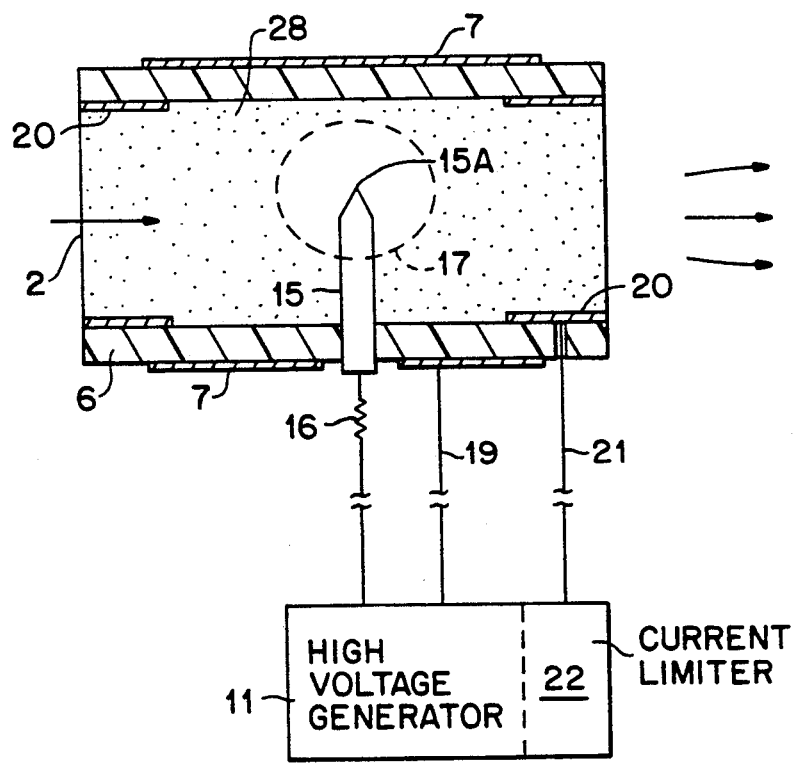
FIG. 2 is a schematic partial cross-section view of the ionizing device employed in the apparatus of FIG. 1.

A conventional commercially obtainable high voltage electrical generator 11 is connected by cable 10, through a suitable plug shown schematically at 10A (in FIG. 1 only), to the ionizing device. Specifically, the generator 11 provides DC output in the 1 to 100 kilovolt range, and is connected electrically to a charging electrode 15 which is supported extending into passage 28, and to conductive cover 7, and to protective conductor rings (later described). Electrode 15 is mounted in the insulating material of body 6, so as to be isolated from conductive covering 7, and terminates in a sharp point or tip 15A which preferably is located centrally of the passage 28 as seen in FIG. 2. The plug connection provides for ready disconnection of ionizer 1 from high voltage generator 11 to allow cleaning, substitution, etc of the ionizer. Typically, cable 10 may be in the order of thirty inches in length.

Electrode point 15A, when the device is energized, produces a high electrical field intensity, generally in the center of the preferably tubular body 6, midway between its inlet and outlet. Numeral 17 indicates the region of a corona discharge which appears around point 15A as the atomizer supplies mist into chamber 28 and the aerosol particles are ionized therewithin. Cable 10 includes a high voltage conductor 18 connected from generator 11 to electrode 15 through a current limiting resistor 16, which has a resistance in the range of 1 to 10 megohms. The outer conductive coating or layer 7 is connected via ground conductor 19 of cable 10 to the DC ground terminal of high voltage generator 11.

This embodiment of the device has been found effective so long as some provision is made to assure that static charges do build up on/in the patient using the apparatus. It appears that in some instances, perhaps due to a variation in the number of particles or droplets present about tip 15A (which could result from flow variations), it is possible for an excess of ions to occur which can result in some charge build up on the patient. Use of ground electrode 7, touched by the patient, dissipates any such charge.

To avoid electrical shock due to accidental or improper insertion of a finger, or some conductive device, into chamber 28 and contact with electrode 15, while the same is energized, a pair of cylindrical conductor rings 20 are provided near the interior edge of inlet 2 and outlet tube 8, and these rings are connected via a conductor 21 in cable 10 to a current limiting circuit 22 of the high voltage generator 11. If a person inadvertently touches or is electrically connected to electrode 15 while the device is energized, the current limiting circuit acts (in known manner) instantaneously to reduce the voltage applied to electrode 15 to ground potential if the current through conductor 21 exceeds ten microamperes, avoiding severe electrical shock to the person. Such current limiting device are per se well known, and further description of their construction and function is not necessary.

The device described has been constructed and tested by applying doses of various medications in aerosol or mist form to mammalian subjects, particularly animals such as dogs. For example, the effectiveness of the inhaled dosage of a labeling agent with and without the above-described ionizing apparatus and method, was tested by excising tissue from dogs used in experiments and measuring the concentrations of a labeling agent in the excised tissue. The following examples sets forth the results of test of the invention on dogs.

EXAMPLE 1

Three greyhound dogs were used as subject animals. One dog served as a control animal, wherein a labeling agent Fluorescein sodium mist was inhaled without mist ionizing device 1, and the other two dogs were administered identical doses of the same mist after it passed through ionizing device 1. Initially, the three dogs were anesthetized using phenobarbital. Each dog was intubated with an American Hospital Supply 8 millimeter endotracheal tube connected to a Puritan-Bennet model m.a. No. 1 mechanical respirator with an Intech MISTI-JET nebulizer attached thereto. Fluorescein sodium was nebulized as a labeling agent for later deposition identification in the three dogs. The three dogs received an intravenous dose of Curari sufficient to paralyze their diaphragms, in order to allow the mechanical respirator to perform their breathing functions for them.

Following the foregoing preparatory procedures, the three dogs were artificially respirated with the mechanical respirator. In each case, the nebulizer was filled with four cubic centimeters of a solution consisting of ten percent Fluorescein sodium 2% and 90% water. The nebulizer was powered by a TULMO-AID air supply system. The mechanical respirator was set to operate at a rate of 20 breaths per minute, with an inspiratory volume of 1200 liters. The three dogs were uniformly respirated with the nebulized aerosol for a continuous 20 minute period. The treatment of the dogs was identical except the aerosol mist for the first dog did not pass through the ionizing device 1, while the aerosol mist did pass through ionizing device 1, with electrode 15 charged to a positive voltage of 25,000 volts, prior to being inhaled by the second and third dogs which were attached to ground potential for the tests.

Following the above procedures, the three dogs were euthanized with a lethal dose of Euthanol by intravenous injection. Autopsies were then performed on the three dogs, and their lungs and trachea were illuminated by ultraviolet light and examined both by naked eye and microscopically for evidence of Fluorscein sodium deposition, which fluoesces under ultraviolet illumination.

The first dog showed no visible evidence of Fluorescein sodium deposition in the lungs. The only evidence of any deposition of Fluorescein sodium appeared on the trachea surface at the point of contact with the cuff of the endotracheal tube and on the cuff itself. The amount of coverage of the trachea by Fluorescein sodium was approximately 40 to 50 square centimeters. In the second and third dogs, the trachea were covered with Fluorescein sodium near the cuff, and deposition of Fluorescein sodium also was obvious throughout the entire trachea and throughout the lungs of those two dogs. Microscopic examination of the alveoli showed a deposition of Fluorescein sodium had occurred throughout the dog's respective lungs.

The above example shows that the method and apparatus will cause ionized medicated mist to be attached to oppositely charged lung tissue so that the medicated mist can be absorbed into the patient's bloodstream, rather than being exhaled and wasted. The effective dose of medication thereby can be much more effectively controlled than for prior mist inhalation devices because of increased adherence of charged medicated mist droplets to lung tissue. The increased adherence will result in increased retention and absorption of the medication by the lungs. The above animal testing results indicates that the mist ionizing apparatus 1 will radically improve the retention and absorption of nebulized aerosol medication in patients with pulmonary diseases and other diseases treatable with nebulized aerosol medication via the respiratory system.

Figure 4:
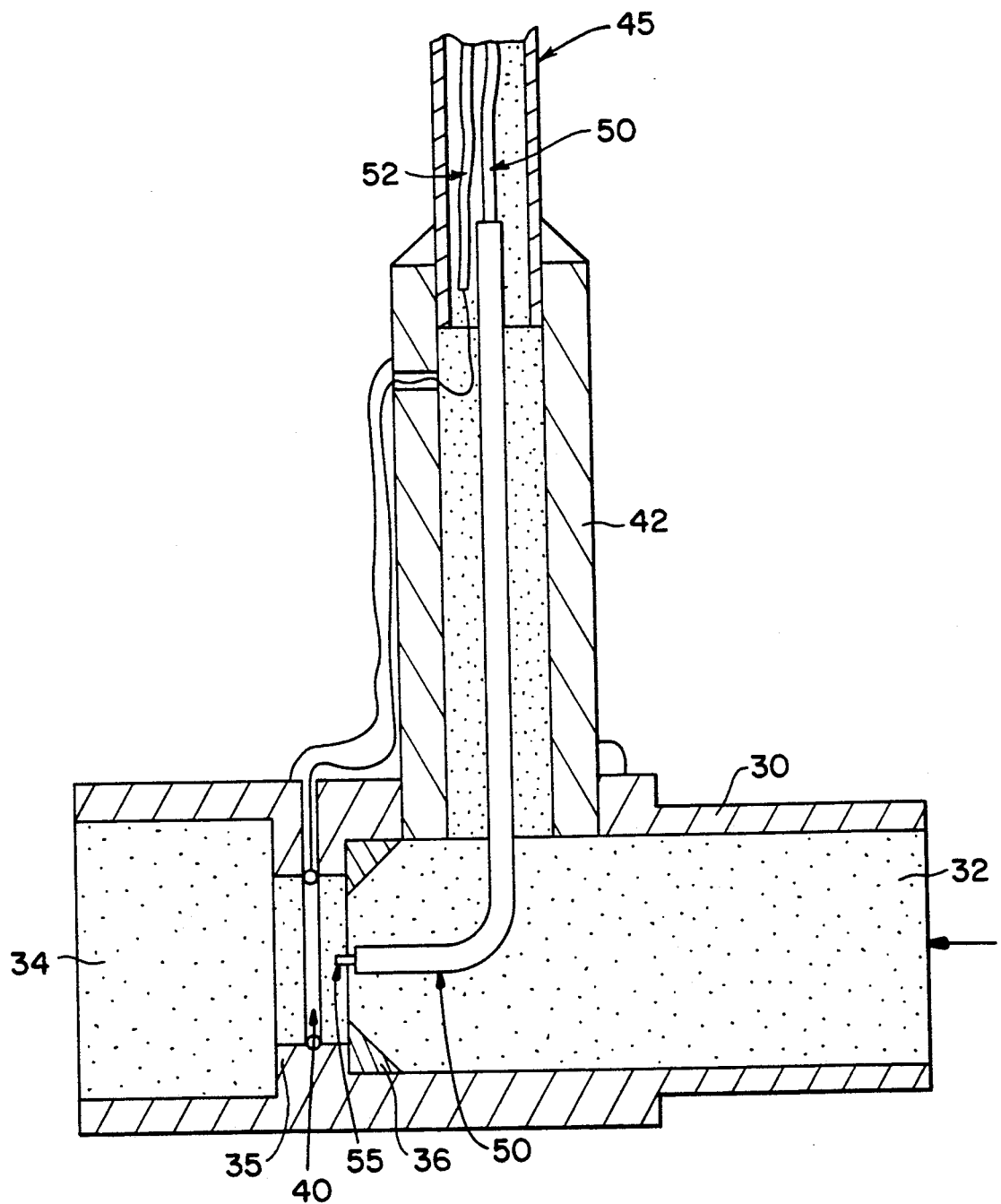
FIG. 4 is an enlarged cross-sectional view of a modification of the device shown in FIG. 3.

Referring to FIG. 4, it has been discovered that contact of the patient with a grounding electrode may be avoided, provided that there is a closely coupled ground electrode in the stream of particulate medication flowed past the charging electrode. It is assumed that the patient/recipient will inherently be at a significantly lower electrical potential than the highly charged medication drops or particles by reason of normal contact with grounded surroundings, and hence the desired polarity difference between recipient's tissue and the positively charged medication will exist. Further, the ground ring will closely or tightly define the charging field, and any unattached electrons return to ground through the ring. Thus, with this embodiment there is not a tendency for build up of a static charge on/in the patient during use of the device.

The device shown in FIG. 4 is intended for use with wet aerosols. Thus a tubular housing 30 incldues an inlet section 32 into which a metered stream of a wet medicated aerosol can be introduced. By this is meant a medication mist or fog of liquid droplets achieved through use of a standard nebulizer or fine spray generator supplied with a liquid medication. Housing 30 also includes an outlet section 34 which may be connected to the patient's mouth or to appropriate conduit extending to the mouth (it is preferred this coupling be short in length), separated by a restriction or central baffle 35, including a tapered inner wall 36, which defines an orifice between the inlet and outlet sections, and tends to increase the velocity of the aerosol particles as they pass through the ion field which is created within a circular electrode 40 mounted in baffle 35, and exposed to the flow of gas and aerosol through the orifice.

A connector tube 42 extends laterally from housing 30 and has connected to it a conduit or hose 45 which provides a supply of drying air from a suitable source (not shown), as well as containing an insulated high voltage lead 50 and an insulated ground return lead 52. The lead and ground return 50,52 are connected to a high voltage generator, and the ground lead 52 is connected to circular electrode 40, while the high voltage lead ends at an electrode tip 55 which is positioned essentially coaxially with circular electrode 40, at the inlet side of the orifice. This arrangement has been found most effective in imparting a charge to the medication droplets in the stream passing around tip 55 and through ground electrode ring 40.

Figure 5:
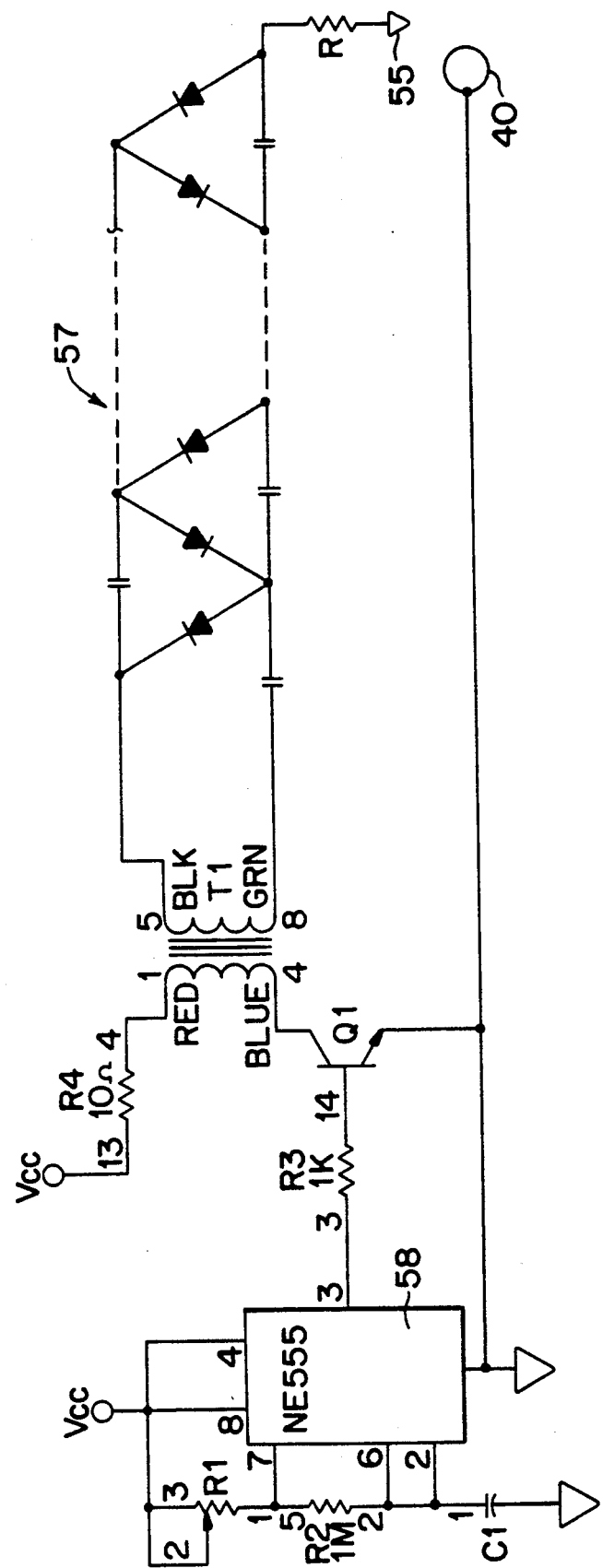
FIG. 5 is a diagram of a high voltage supply circuit for the embodiment of FIG. 4.

FIG. 5 is a schematic diagram of a high voltage power supply suitable for the apparatus shown in FIG. 4. Numeral 57 designates several voltage tripler circuits, indicated as indeterminate in number, which can be added to achieve the desired final high charging potential. The output of circuit 57 is connected through a limiting resistor R to the high voltage electrode tip 55. An integrated circuit timer 58 drives the transistor controlled primary circuit of a step-up transformer, the output of which is coupled to the voltage tripler circuits. Typically, timer provides a triggering output in the order of 40 KHz. This power supply can provide the requisite high voltage, low current charging output from a twelve volt DC input.

Figure 6:
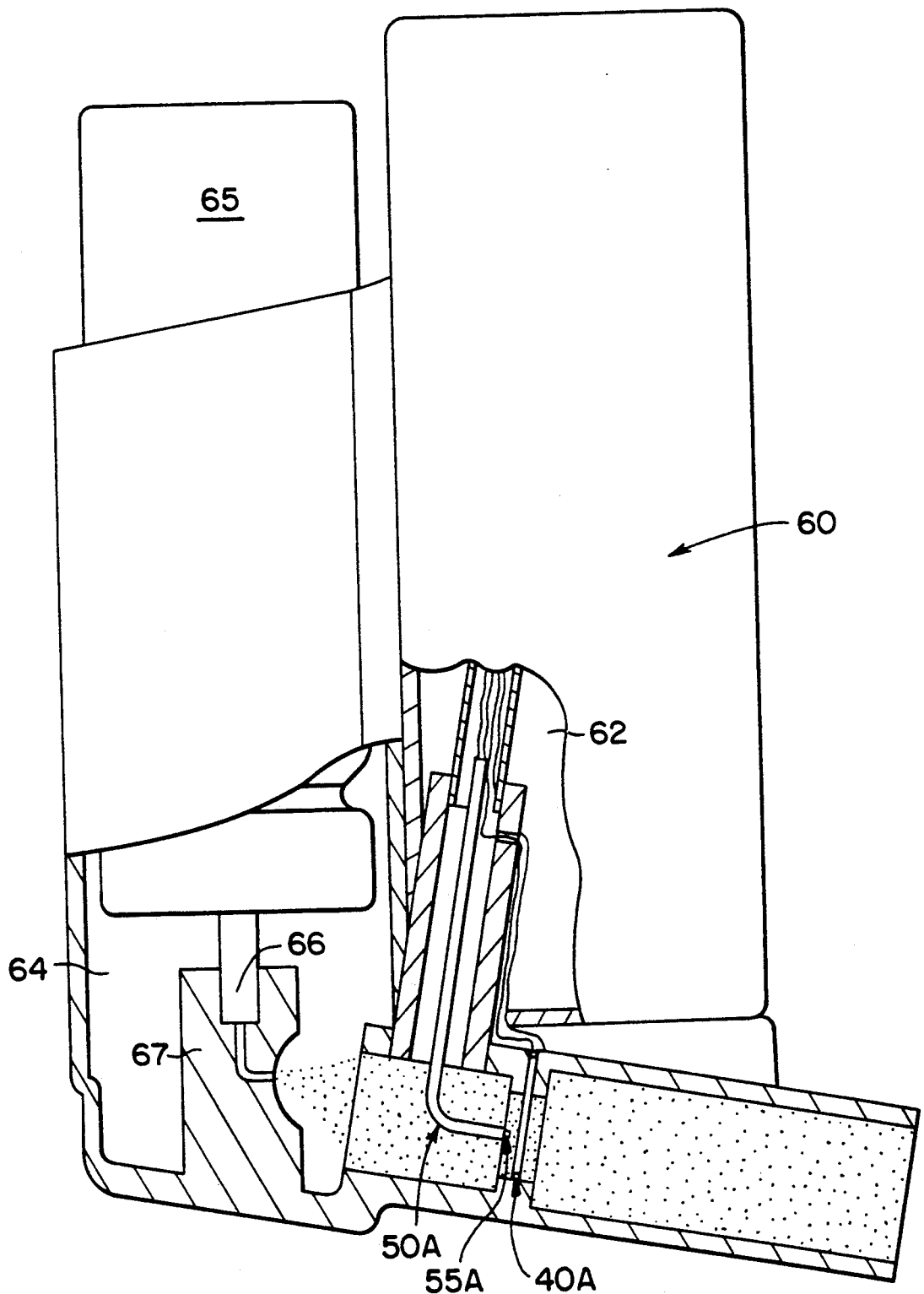
FIG. 6 is an enlarged side view, partially in cross-section, showing a further modification in which the power supply is self-contained, together with a receiver for a metered dose inhaler which expels a dry particle medication.

FIG. 6 shows a modification which uses the electrode arrangement of FIG. 4. In FIG. 6 there is a self-contained housing 60 including a chamber 62 containing a portable high voltage power supply which is connected to a charging electrode tip 55A and to a surrounding ground electrode ring 40A. A second chamber 64 is dimensioned to receive through its open top a typical metered dose inhaler 65 having is tip 66 fitted into a right-angle passage 67, through which medicated powder particles are discharged into the inlet section 32A behind electrode 55A.

While the forms of apparatus and the method have been described with reference to particular embodiments of the invention, which has been successfully tested on mammals as explained, those skilled in the art will be able to make various modifications to the described embodiment without departing from the true spirit and scope of the invention. For example, although only a positive voltage is applied to the electrode in the described embodiment, a negative voltage could be applied to electrode 15 relative to the voltage of ground conductor 19. As long as the body of the patient is suitably grounded relative to the charged medication particles or droplets, providing charged particles causes them to adhere to tissue of a substantially different charge level, causing much more effective utilization of the administered dose, regardless whether the charged mist particles are positive or negative relative to the potential of tissue of the patient's respiratory system.

What is claimed is:

1. A method of uniformly administering medication mist to the lungs of a mammalian patient via inhalation, comprising the steps of
   (a) applying a high voltage, in the order of at least 1000 volts DC, to a pointed electrode located within a passage of an ionizing device having an inlet for connection to a medication aerosol atomizer as a source of medication aerosol mist and an outlet for discharging to the patient's respiratory system, and
   (b) passing the medication mist through the passage of the ionizing device and past the energized electrode to produce an ionized medication mist which can be immediately inhaled from the outlet by the patient,
   (c) electrically grounding the patient relative to the high voltage applied to the electrode to cause the patient's body to be attractive to the charged particles, and
   (d) administering the charged particles to the patient by inhalation while the patient is so electrically grounded whereby charged particles of the medication mist adhere to the patient's lung tissue and other tissue of the patient's respiratory system.

2. The method of claim 1, wherein the ionizing device is provided with a conductive surface member electrically grounded to the high voltage generator, including the step of
   (d) electrically grounding the patient by contact with the conductive surface member of the ionizing device.

3. The method of claim 1, wherein the voltage applied to the electrode is in the order of 5,000 to 50,000 volts DC.

4. A method of uniformly administering medication mist to the lungs of a mammaliam patient via inhalation, comprising the steps of
   (a) applying a high voltage, in the order of at least 1000 volts DC, to a pointed electrode located within a passage of an ionizing device having an inlet for connection to a medication aerosol atomizer as a source of medication aerosol and an outlet for discharging to the patient's respiratory system,
   (b) surrounding the electrode with a grounded ring electrode to define an ion field in the space between the pointed electrode and the ground ring electrode through which the medication aerosol is passed,
   (b) passing the medication mist through the ion field in the ionizing device and thereby producing a medication containing highly charged particles which can be immediately inhaled from the outlet by the patient,
   (c) assuring the patient is maintained at relative electrical ground with respect to the high voltage applied to the electrode to cause the patient's body to be attractive to the charged particles, and
   (d) administering the charged particles to the patient by inhalation whereby charged particles of the medication mist adhere to the patient's lung tissue and other tissue of the patient's respiratory system.

5. An apparatus for administering medication mist to a patient via inhalation, including
   an atomizer providing a source of aerosol medication mist,
   a high voltage DC generator;
   the improvement comprising
   an ionizing device including a housing having wall means defining a chamber and an inlet and outlet to and from said chamber, said inlet being connected to said atomizer for passage of a mist of air-borne medication particles through said chamber and exiting said outlet,
   an electrode having a pointed tip and means supporting said electrode with said tip located within said chamber spaced from and electrically insulated from said wall means, and
   means connecting said high voltage generator to said electrode to electrically charge the particles of mist passing through said chamber,
   a ground electrode supported on a portion of said housing for touching by the patient, and
   means connecting said ground electrode to a ground potential contact on said high voltage generator
   whereby the tissue of the patient's respiratory system is established at ground potential relative to the charged medication particles, and a mist of charged medicated aerosol particles from said outlet of said chamber will be attracted to the tissue of the respiratory system of a patient touching said ground electrode while inhaling the mist from said outlet.

6. Apparatus as defined in claim 5, wherein said electrode tip is located centrally of said chamber spaced approximately equally from said wall means to create an electrical field acting upon all aerosol particles passing through said chamber.

7. Apparatus as defined in claim 6, further comprising conductive ring members located in said chamber between said electrode and said inlet and said outlet, respectively,
   and a current limiting circuit connected to said ring members to prevent harmful electrical shock to a person contacting said electrode when it is energized.

8. An apparatus for administering medication mist to flow from said inlet to said outlet, a patient via inhalation, including
   an atomizer providing a source of aerosol medication mist,
   a high voltage DC generator;
   the improvement comprising
   an ionizing device including a housing having wall means defining a chamber and an inlet and outlet to and from said chamber, said inlet being connected to said atomizer for passage of air-borne medication particles through said chamber and exiting said outlet, a charging electrode having a pointed tip and means supporting said electrode with said tip located within said chamber spaced from and electrically insulated from said wall means, a ground electrode supported within said chamber spaced around said charging electrode and defining therewith an ion field between said electrodes through which the stream of medication aerosol must flow from said inlet to said outlet, and means connecting said high voltage generator to said electrodes to electrically charge the medication particles passing through said chamber, whereby the tissue of the patient's respiratory system is maintained at ground potential relative to the charged medication particles and build up of charge on the patient is avoided while the charged medicated aerosol particles from said outlet of said chamber will be attracted to the tissue of the respiratory system of a patient inhaling the aerosol from said outlet.

* * * * *